(12) United States Patent
Kim (10) Patent No.: US 12,396,624 B2
(45) Date of Patent: Aug. 26, 2025

(54) MULTIFUNCTIONAL CONNECTOR AND ENDOSCOPIC TREATMENT INSTRUMENT HAVING THE SAME

(71) Applicant: Chang Bo Kim, Guri-si (KR)

(72) Inventor: Chang Bo Kim, Guri-si (KR)

(73) Assignee: MENFIS KOREA CO., LTD., Wonju-si (KR)

( * ) Notice: Subject to any disclaimer, the term of this patent is extended or adjusted under 35 U.S.C. 154(b) by 171 days.

(21) Appl. No.: 17/389,980

(22) Filed: Jul. 30, 2021

(65) Prior Publication Data

US 2022/0087511 A1  Mar. 24, 2022

(30) Foreign Application Priority Data

Sep. 23, 2020   (KR) .................. 10-2020-0123270

(51) Int. Cl.
*A61B 1/00* (2006.01)
*A61B 1/12* (2006.01)

(52) U.S. Cl.
CPC ...... *A61B 1/00128* (2013.01); *A61B 1/00119* (2013.01); *A61B 1/126* (2013.01)

(58) Field of Classification Search
CPC ............ A61B 1/00121; A61B 1/00131; A61B 1/0669; A61B 1/01; A61B 1/00128; A61B 1/00119; A61B 1/126; A61B 2017/347; A61B 2017/3447
See application file for complete search history.

(56) References Cited

U.S. PATENT DOCUMENTS

| | | | | |
|---|---|---|---|---|
| 9,974,610 | B2* | 5/2018 | Oguni | A61B 1/00 |
| 10,856,729 | B2* | 12/2020 | Krimsky | A61B 1/00133 |
| 11,337,628 | B2* | 5/2022 | Burkholz | A61M 5/3148 |
| 11,559,646 | B1* | 1/2023 | Osman | A61B 17/3423 |
| 2015/0073211 | A1* | 3/2015 | Dickhans | F16B 2/18 248/229.11 |
| 2016/0143510 | A1* | 5/2016 | Gotoh | A61B 1/00114 600/110 |
| 2018/0310806 | A1* | 11/2018 | Gavalis | A61B 1/00133 |
| 2021/0052148 | A1* | 2/2021 | Hong | A61B 1/00068 |
| 2023/0082615 | A1* | 3/2023 | Kaneko | A61B 34/00 600/104 |

* cited by examiner

*Primary Examiner* — Anh T Nguyen
*Assistant Examiner* — Megan Elizabeth Monahan
(74) *Attorney, Agent, or Firm* — CANTOR COLBURN LLP (57) ABSTRACT

Provided is a multifunctional connector. The multifunctional connector includes an auxiliary conduit which is branched from a main conduit and has a guide portion; and an operation member provided detachably from the auxiliary conduit, wherein the operation member includes an intubation portion inserted into the auxiliary conduit; sliding guide formed to move forward and backward while being guided by the guide portion; a fixing cap fixing the sliding guide so as not to be separated from the guide portion; and a first port through which a fluid is injected or discharged, thereby improving the efficiency of treatment, mitigating the fatigue of medical staffs, and reducing contamination of affected areas and a risk of damage to tissues around an endoscope.

9 Claims, 8 Drawing Sheets

MULTIFUNCTIONAL CONNECTOR AND ENDOSCOPIC TREATMENT INSTRUMENT HAVING THE SAME

BACKGROUND OF THE INVENTION

Field of the Invention

The present disclosure relates to a multifunctional connector, and more particularly, to a multifunctional connector which may be used in combination with an endoscopic treatment instrument.

Description of the Related Art

In general, an endoscopic treatment instrument is used to perform oral treatment using an endoscope. The endoscopic treatment instrument includes a thin and long insertion portion with flexibility, and a treatment portion is provided at a tip of the insertion portion inserted into the human body, and an operation portion operating the treatment portion is installed at an outer draw-out portion of the insertion portion.

Meanwhile, an endoscopic treatment instrument such as a snare, a needle, and a knife may be inserted through a working channel of a flexible endoscope. Here, the snare is used for removing polyps and the like using a trap, the needle is used for injecting a predetermined drug, etc. into an organic tissue, and the knife is used for cutting a predetermined organic tissue such as a lesion.

Thanks to the development of the endoscope, new therapies using the endoscope have been continuously developed, and the development of endoscopic instruments suitable for the new therapies developed as such has been required.

For endoscopic resection, various types of catheter products such as an injection needle, a snare and a knife are used, and these catheter products repeat many times a process of inserting any one catheter product into an endoscopic instrument path, performing the treatment, and then replacing the catheter with another catheter product. A process of inserting a catheter product such as a snare into a thin and long endoscope instrument path, removing the catheter product, and then inserting other instruments, such as injection needles, etc., requires a significant time and efforts. In addition, in conventional endoscopic treatment instruments, a knife, a snare, a needle, an irrigation, and the like are all built into each insert pipe, and as a result, there was a problem that it is difficult to perform the treatment process quickly and a number of treatment assistants are required.

The above-described technical configuration is the background art for helping in the understanding of the present invention, and does not mean a conventional technology widely known in the art to which the present invention pertains.

SUMMARY OF THE INVENTION

An aspect of the present disclosure is to provide a multifunctional connector and an endoscopic treatment instrument with a multifunctional connector in which a plurality of endoscopic treatment instruments are simultaneously inserted to a single cannula to perform different treatments without removing the cannula from the human body while performing an endoscopic treatment, thereby improving the efficiency of treatment, mitigating the fatigue of medical staffs, and reducing contamination of affected areas and a risk of damage to tissues around an endoscope.

According to an exemplary embodiment of the present disclosure, there is provided a multifunctional connector including an auxiliary conduit which is branched from a main conduit and has a guide portion; and an operation member provided detachably from the auxiliary conduit, wherein the operation member includes an intubation portion inserted into the auxiliary conduit; sliding guide formed to move forward and backward while being guided by the guide portion; a fixing cap fixing the sliding guide so as not to be separated from the guide portion; and a first port through which a fluid is injected or discharged, thereby improving the efficiency of treatment.

At this time, the sliding guide is inserted through the inside of the guide portion toward the other side from one side of the guide portion, and the fixing cap is fastened at the end of the sliding guide from the other side of the guide portion to limit a backward range of the sliding guide.

An elastic protrusion is provided on any one of an outer surface of the sliding guide and an inner surface of the guide portion, an engaging jaw is provided on the other surface thereof, and a plurality of elastic protrusions or engaging jaws are provided to be spaced apart from each other, wherein when the sliding guide moves forward or backward along the guide portion, the elastic protrusion is in contact with the engaging jaw, so that the elastic protrusion climbs over the engaging jaw whenever the operation member moves by a predetermined distance.

According to another exemplary embodiment of the present disclosure, there is provided an endoscopic treatment instrument having a multifunctional connector, wherein the cannula is coupled to one end of the main conduit, one end of the liquid delivery tube is coupled to the intubation portion and a hollow needle is coupled to the other end of the liquid delivery tube, at least a portion of the liquid delivery tube is located inside the auxiliary conduit, the main conduit, and the cannula, wherein as the operation member moves forward, the hollow needle moves forward so that the hollow needle protrudes to the outside of the cannula, and as the operation member moves backward, the hollow needle moves backward so that the hollow needle is introduced into the cannula.

In addition, an electrode operating device for treatment is coupled to the other end of the main conduit, wherein the electrode operating device for treatment includes a slider sliding along a body; a first handle provided at one side of the body; a second handle provided in the slider; a shaft of which one end is coupled to the slider; and a treatment electrode provided at the other end of the shaft.

In addition, at least a portion of the shaft is located inside the main conduit and the cannula, as the slider moves forward, the treatment electrode moves forward so that the treatment electrode protrudes to the outside of the cannula, and as the slider moves backward, the treatment electrode moves backward so that the treatment electrode is introduced into the cannula.

The endoscopic treatment instrument may further include a knob coupled to one side of the shaft to rotate the shaft; a knob housing that rotatably couples the knob to the body; and an electrode connector provided in the slider.

The endoscopic treatment instrument may further include a rotary housing provided at the other end of the main conduit; and a rotary connector provided at the other side of the body, wherein a head receiving portion is provided in the rotary housing, and a rotary guide groove is formed by passing through the inside and the outside of the rotary housing, the rotary connector is provided with a head portion inserted into the head receiving portion, and a protrusion is provided on the outer surface of the head portion, the head portion is inserted into the head receiving portion while the protrusion slides to be in contact with the sliding groove provided in the head receiving portion and the rotary connector is rotated while the protrusion is guided to be in contact with the rotary guide groove.

According to the embodiment of the present disclosure, a plurality of endoscopic treatment instruments are simultaneously inserted to a single cannula to perform different treatments without removing the cannula from the human body while performing an endoscopic treatment, thereby improving the efficiency of treatment, mitigating the fatigue of medical staffs, and reducing contamination of affected areas and a risk of damage to tissues around an endoscope. Further, since a treatment instrument such as an injection needle is inserted to precisely adjust a protrusion degree of the needle and the treatment instrument such as an injection needle is separated to inject a cleaning liquid through the inside of the cannula, there is no need to separate the cannula from the human body while alternately performing the treatment process and the cleaning process using the injection needle, thereby significantly reducing the contamination of affected areas and a risk of damage to tissues around an endoscope which may occur in a process of replacing equipment.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Advantages and features of the present disclosure, and methods for accomplishing the same will be more clearly understood from exemplary embodiments described in detail below with reference to the accompanying drawings. However, the present disclosure is not limited to embodiments disclosed below but may be implemented in various different forms. The present embodiments are provided so that the disclosure of the present disclosure may not only be complete, but also may fully provide the scope of the present disclosure to those skilled in the art. Throughout the whole specification, the same reference numerals denote the same elements.

It is also to be understood that the terminology used herein is for the purpose of describing embodiments only and is not intended to limit the present disclosure. In this specification, singular forms include even plural forms unless the context indicates otherwise. It is to be understood that the terms 'comprise' and/or 'comprising' used in the specification are intended to be inclusive in a manner that does not exclude the presence of stated components, steps, operations, and/or elements does not exclude the addition.

Hereinafter, a configuration and an operation effect of the present disclosure will be described in more detail with reference to the accompanying drawings.

Figure 1:
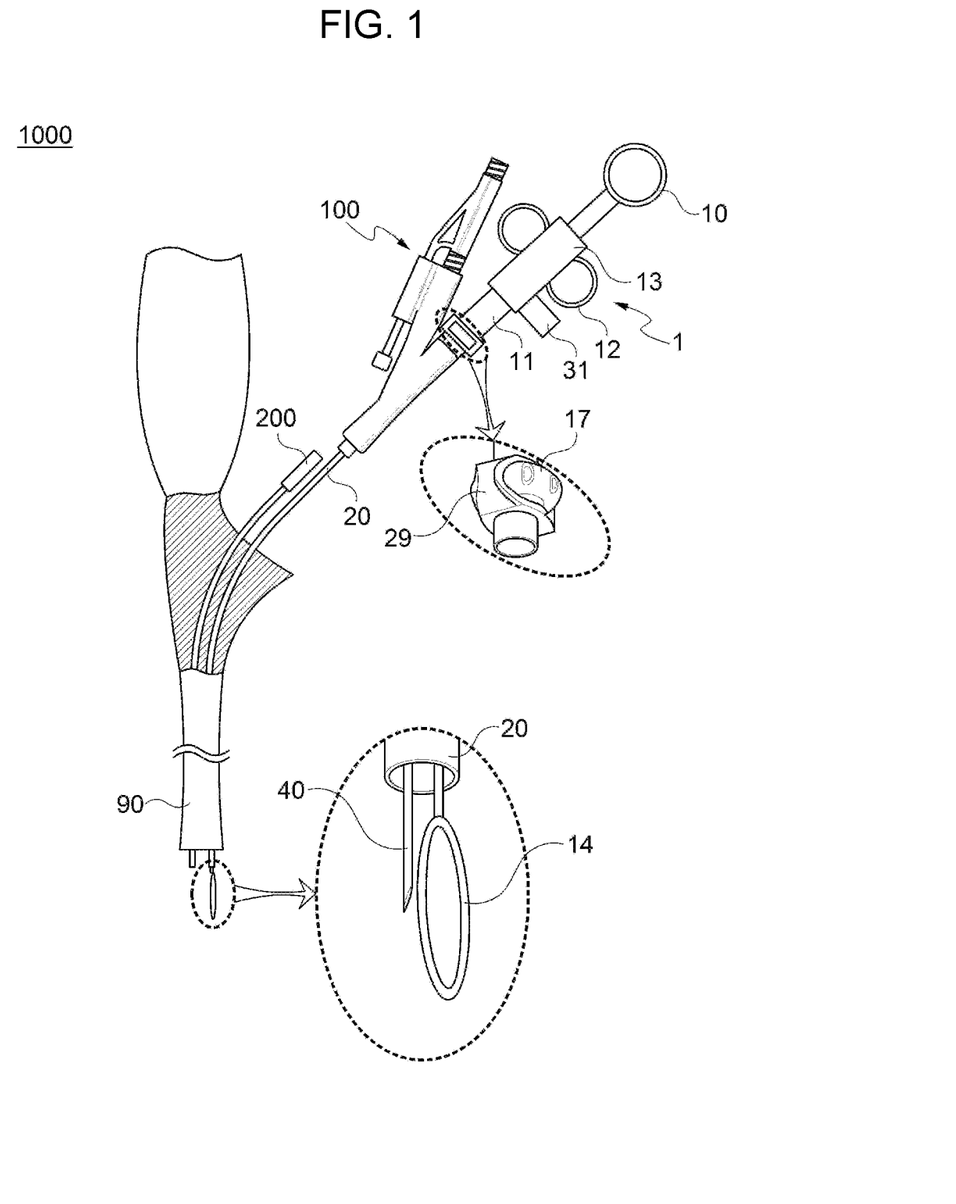
FIG. 1 is a diagram for describing an endoscopic treatment instrument having a multifunctional connector according to an embodiment of the present disclosure.
Figure 2:
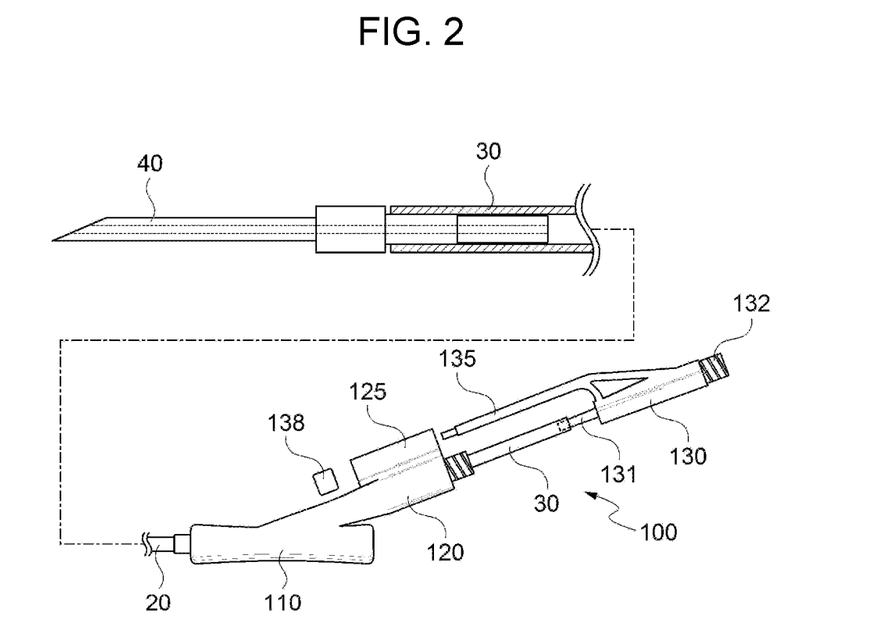
FIG. 2 is a diagram for describing a multifunctional connector according to an embodiment of the present disclosure.
Figure 3:
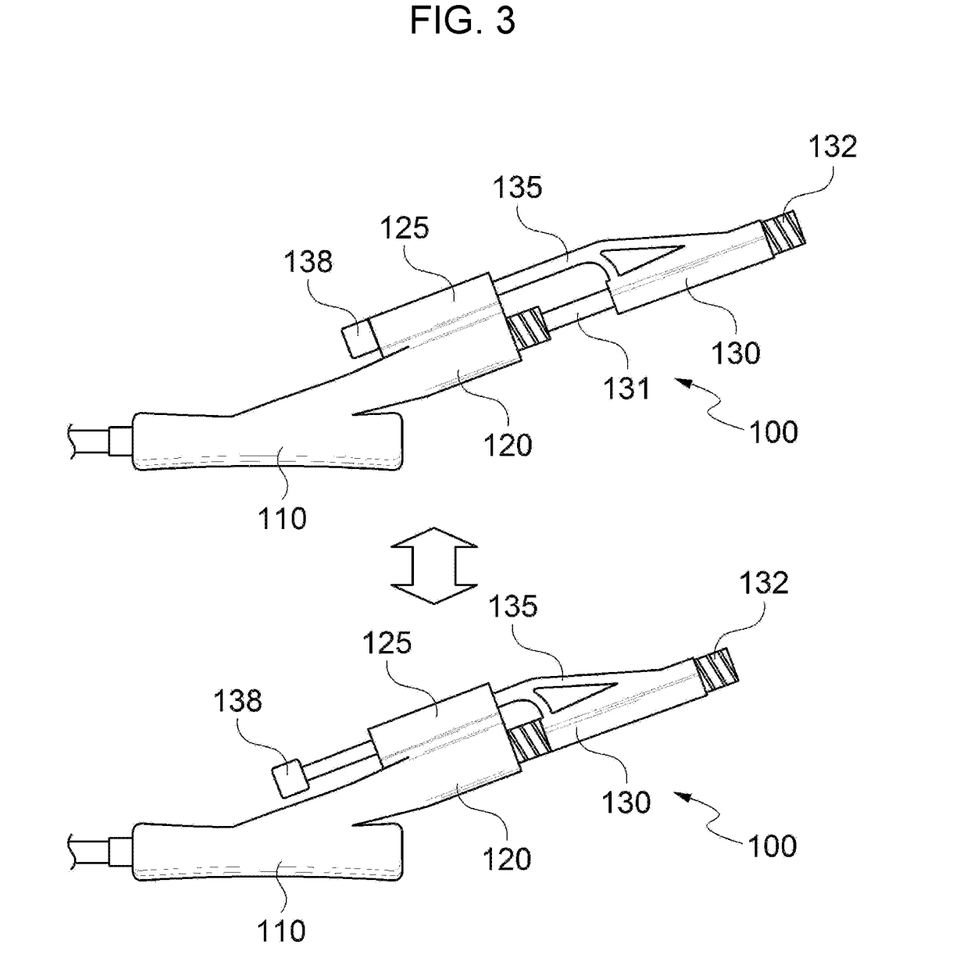
FIG. 3 is a diagram for describing an operational principle of the multifunctional connector according to an embodiment of the present disclosure.
Figure 4:
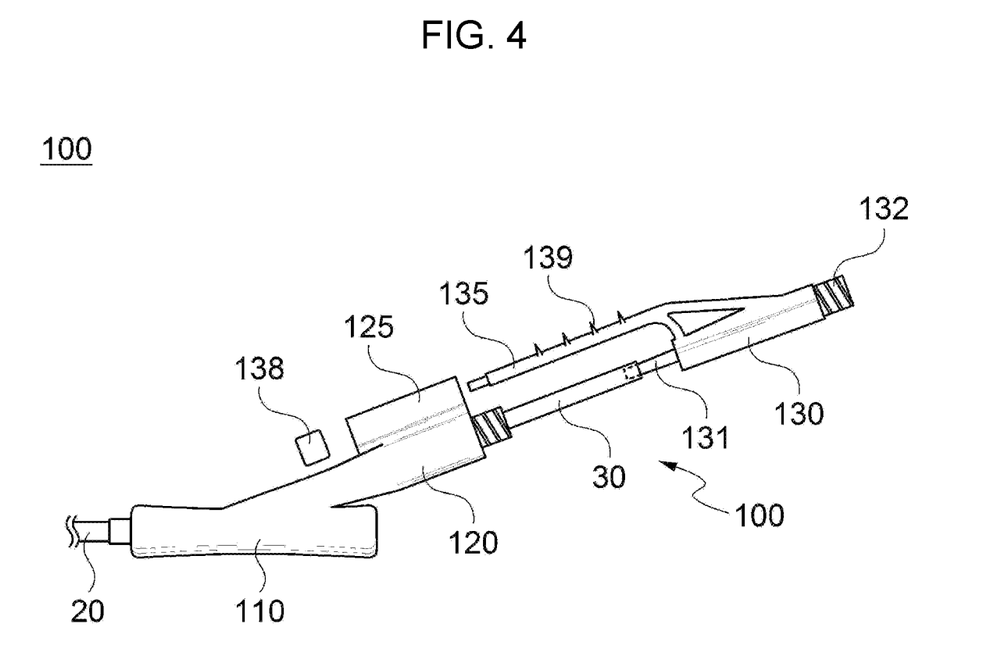
FIG. 4 is a diagram for describing an operating method of the multifunctional connector according to an embodiment of the present disclosure.
Figure 5:
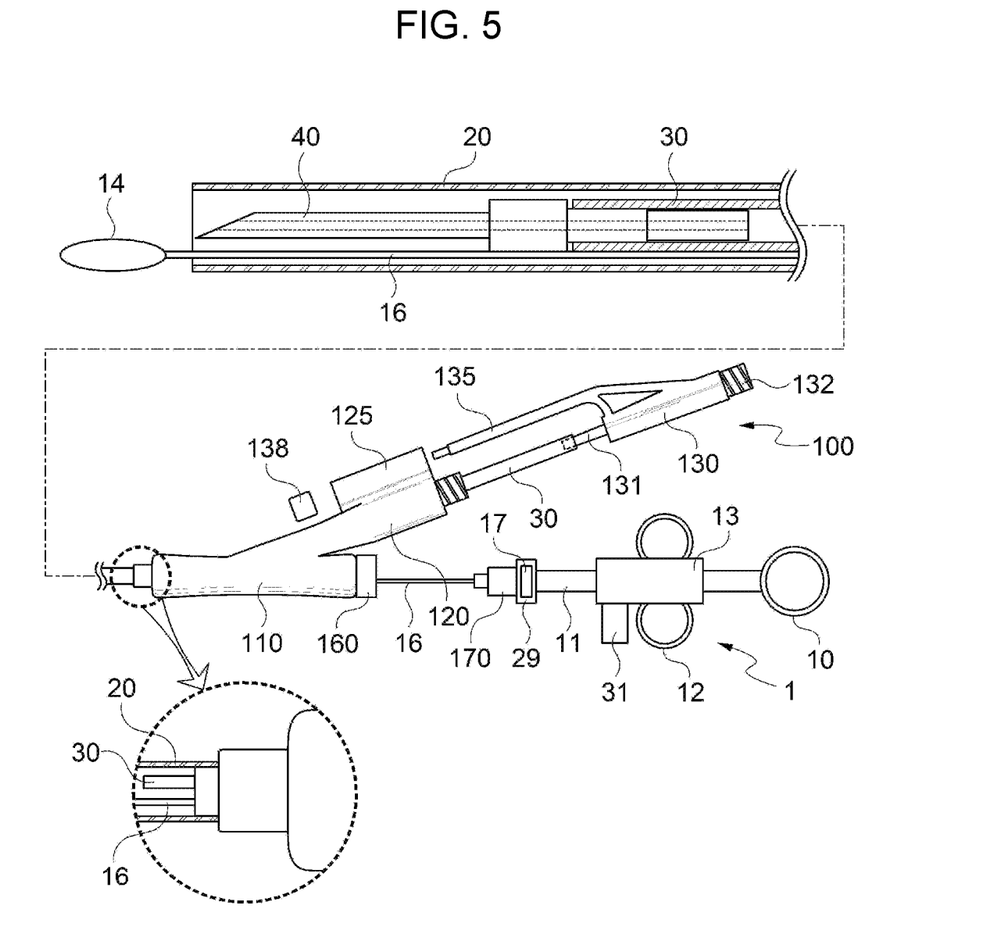
FIG. 5 is a diagram for describing an endoscopic treatment instrument having a multifunctional connector according to an embodiment of the present disclosure.
Figure 6:
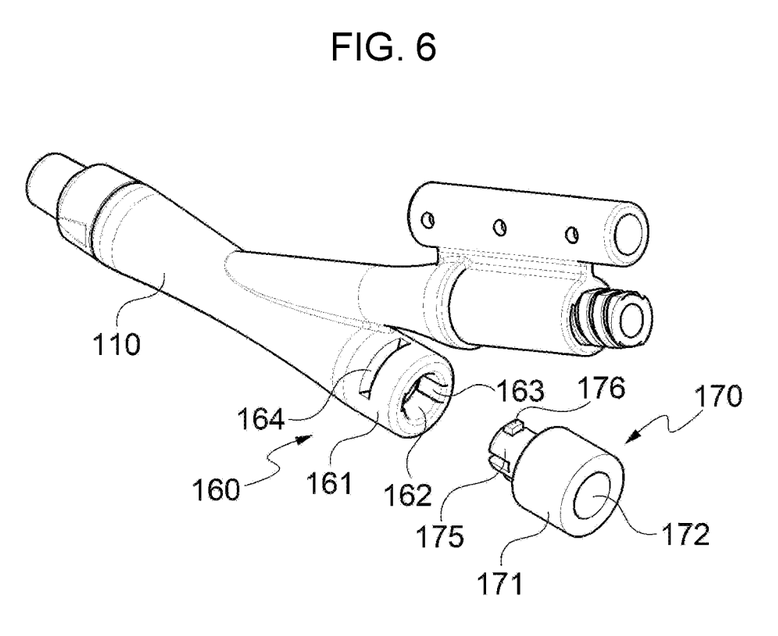
FIG. 6 is a diagram for describing a multifunctional connector according to an embodiment of the present disclosure.
Figure 7:
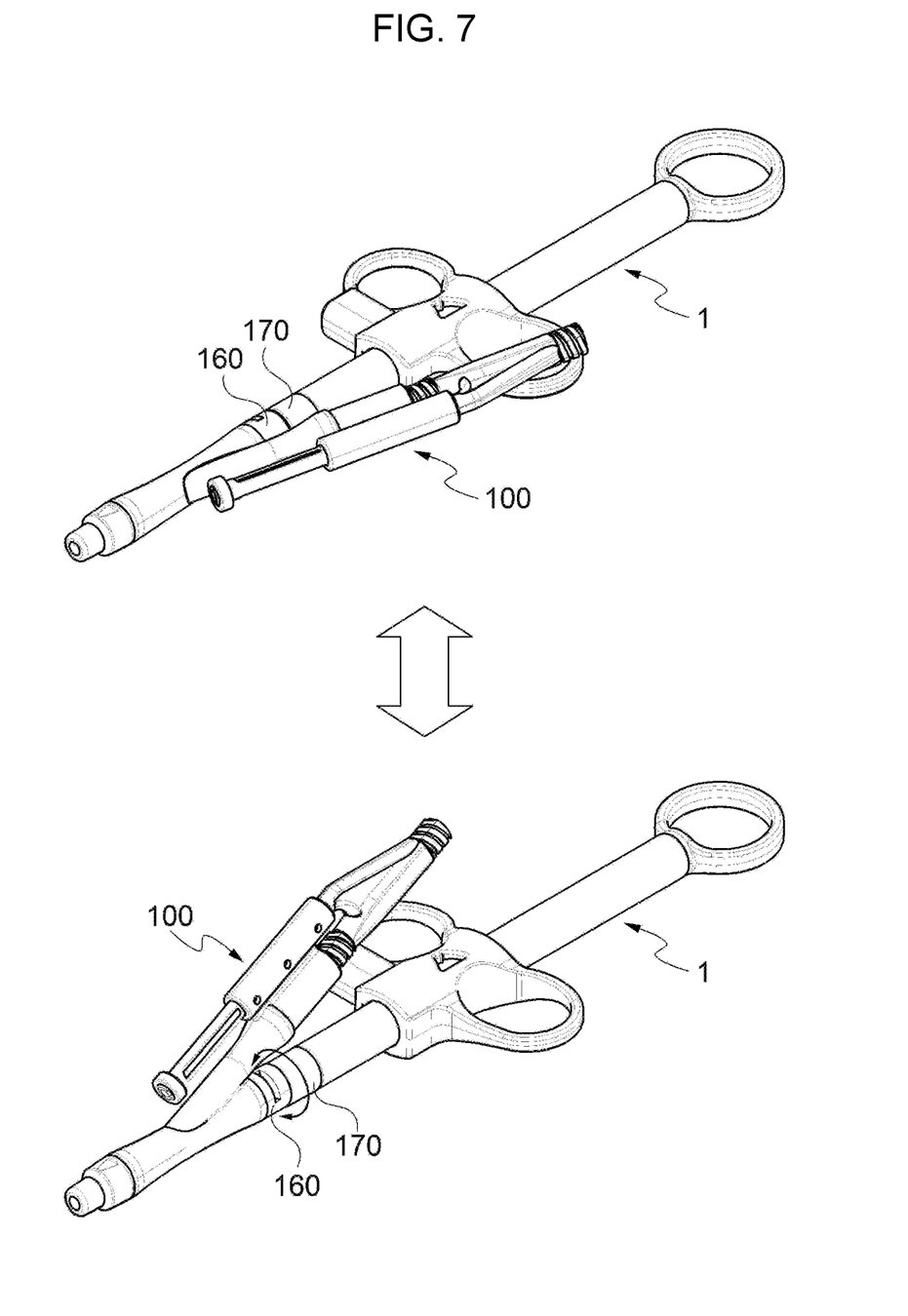
FIG. 7 is a diagram for describing an operational principle of the endoscopic treatment instrument using the multifunctional connector illustrated in FIG. 6.
Figure 8:
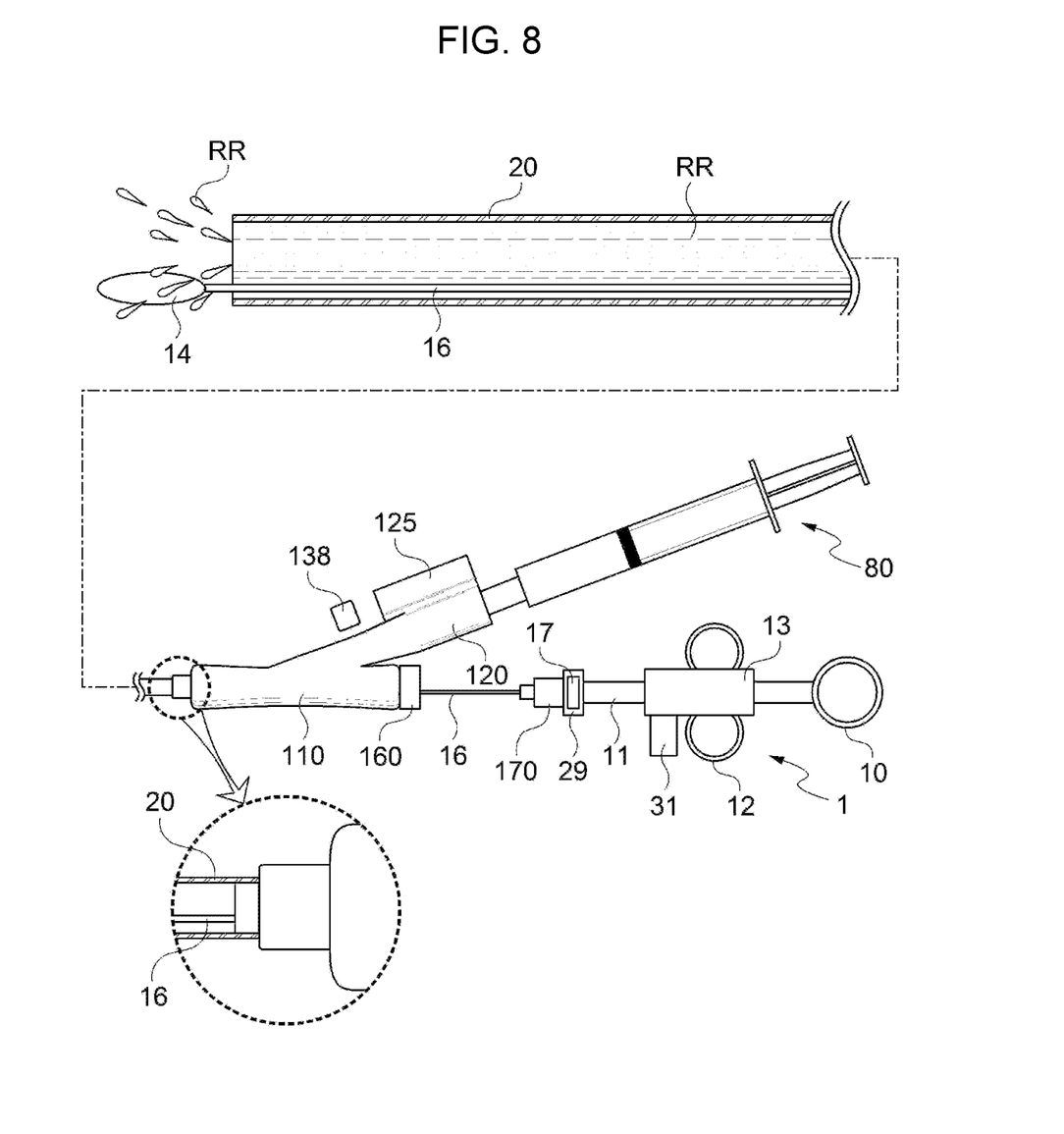
FIG. 8 is a diagram for describing an application method of the endoscopic treatment instrument having the multifunctional connector according to an embodiment of the present disclosure.

FIG. 1 is a diagram for describing an endoscopic treatment instrument 1000 having a multifunctional connector according to an embodiment of the present disclosure, FIG. 2 is a diagram for describing a multifunctional connector 100 according to an embodiment of the present disclosure, FIG. 3 is a diagram for describing an operational principle of the multifunctional connector 100 according to an embodiment of the present disclosure, FIG. 4 is a diagram for describing an operating method of the multifunctional connector 100 according to an embodiment of the present disclosure, FIG. 5 is a diagram for describing an endoscopic treatment instrument 1000 having a multifunctional connector according to an embodiment of the present disclosure, FIG. 6 is a diagram for describing a multifunctional connector 100 according to an embodiment of the present disclosure, FIG. 7 is a diagram for describing an operational principle of the endoscopic treatment instrument using the multifunctional connector 100 illustrated in FIG. 6, and FIG. 8 is a diagram for describing an application method of the endoscopic treatment instrument 1000 having the multifunctional connector according to an embodiment of the present disclosure.

Referring to FIG. 1, a cannula 20 of an endoscopic treatment instrument 1000 having a multifunctional connector according to an embodiment of the present disclosure may be inserted into an endoscopic tube 90 of endoscopic equipment, and a separate endoscopic treatment device 200 may be further inserted into the endoscopic tube 90.

Referring to the drawings, a multifunctional connector 100 according to an embodiment of the present disclosure includes a main conduit 110, an auxiliary conduit 120, and an operation member 130. The cannula 20 is coupled to one end of the main conduit 110 and an endoscopic treatment instrument such as an electrode operation device 1 for treatment, and a knife (not illustrated) may be connected to the main conduit 110. The auxiliary conduit 120 is branched from the main conduit 110 and various treatment instruments such as an injection needle, a syringe 80 for injecting a cleaning liquid may be connected through the auxiliary conduit 120. Accordingly, the treatment instrument such as the electrode operation device 1 for treatment or the knife connected to the main conduit 110 and the treatment instrument such as the injection needle connected to the auxiliary conduit 120 may share the main conduit 110 and the cannula 20, and a plurality of treatment instruments are inserted into the human body through one cannula 20 to be used for treatment.

In one embodiment, the auxiliary conduit 120 is provided with a guide portion 125, and while a sliding guide 135 of the operation member 130 is guided by the guide portion 125, the operation member 130 may be configured to move forward or backward. Further, the operation member 130 is provided with an intubation portion 131 and a first port 132. A liquid delivery tube 30 of the injection needle and the like may be coupled to the intubation portion 131, and the liquid delivery tube 30 may be inserted to the multifunctional connector 100 to sequentially pass through the auxiliary conduit 120, the main conduit 110, and the cannula 20. Further, a hollow needle 40 may be coupled to an end of the liquid delivery tube 30 and a liquid injected through the first port 132 may be discharged through the hollow needle 40 via the liquid delivery tube 30. Meanwhile, as the operation member 130 moves forward or backward, the hollow needle 40 may protrude to the outside of the cannula 20 or be introduced into the cannula 20. Further, the protruding degree of the hollow needle 40 may be precisely adjusted according to the forward or backward degree of the operation member 130. The multifunctional connector 100 according to an embodiment of the present disclosure may move forward or backward while the sliding guide 135 of the operation member 130 is guided by the guide portion 125 of the auxiliary conduit 120, so that a precise and stable operation is enabled in the process of moving the operation member 130 forward or backward. In one embodiment, the sliding guide 135 may be inserted through the inside of the guide portion 125 toward the other side from one side of the guide portion 125. A fixing cap 138 may be fastened to the end of the sliding guide 135 which is inserted through the guide portion 125. Accordingly, after the sliding guide 135 moves backward and then does not move backward any longer after the fixing cap 138 is in contact with the guide portion 125, and as a result, a backward range of the operation member 130 may be limited. Accordingly, in the process of moving the operation member 130 backward, the operation member 130 may need not to be careful so as not to excessively move backward, thereby improving the convenience and efficiency of the treatment. Meanwhile, the fixing cap 138 may be detachably coupled to the sliding guide 135 and when the fixing cap 138 is removed, the sliding guide 135 may be completely separated from the guide portion 125.

Referring to FIG. 4, an elastic protrusion 139 is provided in the sliding guide 135 and an engaging jaw may be provided on the guide portion 125, and when the sliding guide 135 moves forward or backward along the guide portion 125, the elastic protrusion 139 may be selectively in contact with the engaging jaw. Accordingly, whenever the operation member 130 moves at a predetermined distance, the elastic protrusion 139 climbs over the engaging jaw, and in this process, a predetermined sound occurs or a vacuum may occur in the operation member 130 or the main conduit 110, so that an operator may efficiently grasp the forward degree of the operation member 130 by using the sound or vacuum. In the drawings, the embodiment in which the elastic protrusion 139 is provided in the sliding guide 135 is illustrated, but the engaging jaw is provided in the sliding guide 135 and the elastic protrusion 139 may be provided in the guide portion 125.

In the endoscopic treatment instrument 1000 having the multifunctional connector according to an embodiment of the present disclosure, the cannula 20 is coupled to one end of the main conduit 110. One end of the liquid delivery tube 30 is coupled to the intubation portion 131 of the operation member 130, and the hollow needle 40 is coupled to the other end of the liquid delivery tube 30. At this time, at least a portion of the liquid delivery tube 30 is located inside the auxiliary conduit 120, the main conduit 110, and the cannula 20. Accordingly, when the operation member 130 moves forward or backward, the liquid delivery tube 30 and the hollow needle 40 move forward or backward.

In one embodiment as shown in FIG. 5, the electrode operation device 1 for treatment may be coupled to the other end of the main conduit 110. The electrode operation device 1 for treatment may include a body 11, a slider 13, a first handle 10, a second handle 12, and a shaft 16. The slider 13 is slid along the body 11 having the first handle 10 on one side and the second handle 12 is provided in the slider 13. Further, one end of the shaft 16 is coupled to the slider 13, and the other end of the shaft 16 is provided with a snare. Here, the shaft 16 may be located inside the main conduit 110 and the cannula 20 and when the slider 13 moves forward, a treatment electrode 14 protrudes to the outside of the cannula 20 and when the slider 13 moves backward, the snare is introduced into the cannula 20. An electrode connector 31 may be provided in the slider, and a current applied through the electrode connector 31 may be applied to the treatment electrode 14 through the shaft 16. Meanwhile, a knob housing 29 is provided at the other side of the body 11, and at least a portion of the shaft 16 may be coupled to a knob 17 rotatably coupled to the knob housing 29. Accordingly, when the knob housing 29 is rotated, the treatment electrode 14 may be rotated as the shaft 16 is rotated.

In one embodiment, the treatment electrode 14 may refer to terminology that collectively refers to a snare, a knife portion, or the like.

In one embodiment, a snare device in which the snare is applied as the treatment electrode 14 may be used as the electrode operation device 1 for treatment.

In another embodiment, a knife device in which a knife portion having a metal rod shape is applied as the treatment electrode 14 may be used as the electrode operation device 1 for treatment.

Referring to FIGS. 5 and 6, a rotary housing 160 is provided at the other end of the main conduit 110 and a rotary connector 170 may be provided at the other side of the body 11. At this time, in the rotary housing 160, a head receiving portion 162 and a rotary housing 160 may be provided. The rotary housing 160 may be provided with a rotary guide groove 164 passing through the inside and the outside thereof. On the other hand, the rotary connector 170 is provided with a head portion 175 inserted into the head receiving portion 162, and a protrusion 176 may be provided on the outer surface of the head portion 175. Further, a connection portion 171 having a receiving groove 172 may be provided on the rear side of the head portion 175, and one end of the body may be inserted into the receiving groove 172. The head portion 175 may be inserted into the head receiving portion 162 while the protrusion 176 slides to be in contact with the sliding groove 163 provided in the head receiving portion 162. In addition, the rotary connector 170 may be rotated while the protrusion 176 is guided to be in contact with the rotary guide groove 164. Accordingly, as illustrated in FIG. 7, the multifunctional connector 100 may be rotated according to the rotation of the rotary housing 160 and the rotary connector 170. At the time of storage, the multifunctional connector 100 is rotated so that the operation member 130 is close to the electrode operating device 1 for treatment to ensure the convenience of storage. During the treatment, the multifunctional connector 100 is rotated so that the operation member 130 is far away from the electrode operating device 1 for treatment, and as a result, the operating process of the electrode operating device 1 for treatment and the operating process of the operation member 130 may be smoothly performed without interference.

Referring to FIG. 8, while the operation member 130, the liquid delivery tube 30, and the hollow needle 40 are removed from the multifunctional connector 100, a syringe 80 may be connected to the auxiliary conduit 120, and a cleaning liquid RR is injected using the syringe 80 to efficiently perform the cleaning process in the treatment process using the electrode operating device 1 for treatment.

An endoscopic treatment instrument having a multifunctional connector according to an embodiment of the present disclosure includes an auxiliary conduit which is branched from a main conduit of which a cannula is coupled to one end and has a guide portion; an operation member which includes an intubation portion provided to be insertable into the auxiliary conduit, a sliding guide provided to be spaced apart from the intubation portion and formed to move forward and backward while being guided by the guide portion, a fixing cap fixing the sliding guide so as not to be separated from the guide portion, and a first port through which a fluid is injected or discharged and is provided detachably from the auxiliary conduit; a syringe provided detachably from the auxiliary conduit and storing a cleaning liquid, and a liquid delivery tube of which one end is connected to the intubation portion and the other end is coupled to a hollow needle. One of the operation member and the syringe is selected to be coupled to the auxiliary conduit, and when the operation member is coupled to the auxiliary conduit, at least a portion of the liquid delivery tube is located inside the auxiliary conduit, the main conduit, and the cannula. As a result, as the operation member moves forward, the hollow needle moves forward so that the hollow needle protrudes to the outside of the cannula, and as the operation member moves backward, the hollow needle moves backward so that the hollow needle is introduced into the cannula. In addition, when the syringe is coupled to the auxiliary conduit to inject the cleaning liquid, the cleaning liquid may be injected through the auxiliary conduit and the cannula.

Therefore, the scope of the present disclosure should not be limited to the embodiments and should be defined by the appended claims and equivalents to the appended claims.

In other words, the embodiments described above are illustrative in all aspects and should be understood as not being restrictive, and the scope of the present disclosure is represented by appended claims to be described below rather than the detailed description, and it is to be interpreted that the meaning and scope of the appended claims and all changed or modified forms derived from the equivalents thereof are included within the scope of the present disclosure.

What is claimed is:

1. A multifunctional connector comprising:
    an auxiliary conduit branched from a main conduit and having a guide portion integrally formed with the auxiliary conduit; and
    an operation member detachably coupled to the auxiliary conduit, wherein the operation member comprises:
        an intubation portion inserted into the auxiliary conduit;
        a sliding guide inserted into the guide portion and configured to move forward and backward while being guided by the guide portion;
        a fixing cap fixing the sliding guide so as not to be separated from the guide portion; and
        a first port connected with the intubation portion, wherein a fluid is injected or discharged through the first port and the fluid passes through the intubation portion, and
    wherein the sliding guide passes through the guide portion from a first side of a guide conduit of the guide portion toward a second side of the guide conduit of the guide portion,
    the guide conduit of the guide portion is parallel to and spaced apart from the auxiliary conduit so that the sliding guide moves parallel to and spaced apart from the intubation portion, and
    the fixing cap is fastened at a distal end face of the sliding guide from the second side of the guide conduit of the guide portion and configured to limit a backward range of the sliding guide as an end face of the fixing cap abuts the guide portion while the sliding guide moves forward and backward.

2. The multifunctional connector of claim 1, further comprising:
    a cannula coupled to a first end of the main conduit; and
    a liquid delivery tube, one portion of the liquid delivery tube is disposed inside the cannula,
    wherein another portion of the liquid delivery tube is disposed inside the auxiliary conduit,
    one end of the liquid delivery tube is coupled to the intubation portion, and
    the fluid passes through inside the liquid delivery tube.

3. The multifunctional connector of claim 1, further comprising: a plurality of elastic protrusions formed on an outer surface of the sliding guide or on an inner surface of the guide conduit of the guide portion and a plurality of engaging jaws formed on the inner surface of the guide conduit of the guide portion or on the outer surface of the sliding guide, the plurality of elastic protrusions and the plurality of engaging jaws being spaced apart from each other, wherein when the sliding guide moves forward or backward along the guide portion, the plurality of elastic protrusions are in contact with the plurality of engaging jaws, so that the plurality of elastic protrusions climb over the plurality of engaging jaws whenever the operation member moves by a predetermined distance.

4. The multifunctional connector of claim 2, further comprising:
    a rotary housing provided at a second end of the main conduit; and
    a rotary connector comprising a first end and a second end, wherein the first end is coupled to the rotary housing and the second end is coupled with a treatment instrument,
    wherein a head receiving portion is provided in the rotary housing, and a rotary guide groove passing through the rotary housing is formed,
    the rotary connector is provided with a head portion inserted into the head receiving portion, and a protrusion is provided on an outer surface of the head portion,
    the head portion is inserted into the head receiving portion while the protrusion slides to be in contact with a sliding groove provided inside the head receiving portion and the rotary connector is rotated while the protrusion is guided to be in contact with the rotary guide groove.

5. An endoscopic treatment instrument having a multifunctional connector comprising:
    a main conduit comprising a first end coupled to a cannula, an auxiliary conduit branched from the main conduit and having a guide portion integrally formed with the auxiliary conduit;

an operation member including an intubation portion provided to be insertable into the auxiliary conduit, a sliding guide provided to be spaced apart from the intubation portion and configured to move forward and backward while being guided by the guide portion, a fixing cap fixing the sliding guide so as not to be separated from the guide portion, and a first port connected with the intubation portion, wherein a fluid is injected or discharged through the first port; and a liquid delivery tube having a first end coupled to the intubation portion and having a hollow needle coupled to a second end of the liquid delivery tube, wherein the sliding guide passes through the guide portion from a first side of a guide conduit of the guide portion toward a second side of the guide conduit of the guide portion, and the guide conduit of the guide portion is parallel to and spaced apart from the auxiliary conduit so that the sliding guide moves parallel to and spaced apart from the intubation portion, the fixing cap is fastened at a distal end face of the sliding guide from the second side of the guide conduit of the guide portion and configured to limit a backward range of the sliding guide as an end face of the fixing cap abuts the guide portion while the sliding guide moves forward and backward, wherein the operation member detachably coupled to the auxiliary conduit, wherein, when the operation member is coupled to the auxiliary conduit, at least a portion of the liquid delivery tube is located inside the auxiliary conduit, the main conduit, and the cannula, and wherein, as the operation member moves forward, the hollow needle moves forward so that the hollow needle is introduced into protrudes out of the cannula, and as the operation member moves backward, the hollow needle moves backward so that the hollow needle moves out from retracts into the cannula.

6. The endoscopic treatment instrument having the multifunctional connector of claim 5, wherein an electrode operating device for treatment is coupled to a second end of the main conduit, and wherein the electrode operating device for treatment comprises:

a body;

a slider sliding along the body;

a first handle provided at one side of the body;

a second handle provided in the slider;

a shaft, a first end of which is coupled to the slider; and a treatment electrode provided at a second end of the shaft.

7. The endoscopic treatment instrument having the multifunctional connector of claim 6, wherein at least a portion of the shaft is located inside the main conduit and the cannula, wherein, as the slider moves forward, the treatment electrode moves forward so that the treatment electrode protrudes into the cannula, and wherein, as the slider moves backward, the treatment electrode moves backward so that the treatment electrode moves out from the cannula.

8. The endoscopic treatment instrument having the multifunctional connector of claim 6, wherein the electrode operating device for treatment further comprises:

a knob coupled to one side of the shaft to rotate the shaft;

a knob housing that rotatably couples the knob to the body; and an electrode connector provided in the slider.

9. The endoscopic treatment instrument having the multifunctional connector of claim 6, further comprising:

a rotary housing provided at the first end of the main conduit; and a rotary connector, one end of which is coupled to the rotary housing, wherein a head receiving portion is provided in the rotary housing, and a rotary guide groove passing through the rotary housing is formed, the rotary connector is provided with a head portion inserted into the head receiving portion, and a protrusion is provided on an outer surface of the head portion, the head portion is inserted into the head receiving portion while the protrusion slides to be in contact with a sliding groove provided inside the head receiving portion and the rotary connector is rotated while the protrusion is guided to be in contact with the rotary guide groove.

* * * * *